United States Patent [19]

Brown et al.

[11] Patent Number: 5,494,922

[45] Date of Patent: Feb. 27, 1996

[54] ALLOPHANIC ACID DERIVATIVES

[75] Inventors: George R. Brown, Wilmslow; Richard E. Shute, Macclesfield, both of United Kingdom

[73] Assignee: Zeneca Limited, London, England

[21] Appl. No.: 462,024

[22] Filed: Jun. 5, 1995

Related U.S. Application Data

[62] Division of Ser. No. 365,761, Dec. 29, 1994, which is a continuation of Ser. No. 266,454, Jun. 27, 1994, abandoned.

[30] Foreign Application Priority Data

Jun. 28, 1993 [GB] United Kingdom ............... 9313269

[51] Int. Cl.⁶ .................... A61K 31/44; A01N 43/40
[52] U.S. Cl. .................. 514/352; 528/44; 528/48; 528/271; 528/274; 528/288; 528/289; 528/292; 528/298; 528/299; 528/335; 528/367; 528/368; 514/553; 514/579; 514/583; 546/297; 546/300; 546/332
[58] Field of Search ................... 528/44, 48, 271, 528/274, 288, 289, 292, 298, 299, 335, 367, 368; 514/352, 553, 579, 583; 546/297, 300, 332

[56] References Cited

U.S. PATENT DOCUMENTS

| | | | |
|---|---|---|---|
| 4,665,235 | 5/1987 | Brouwer et al. | 564/44 |
| 4,710,516 | 12/1987 | Brouwer et al. | 514/594 |
| 5,039,805 | 8/1991 | Alig et al. | 546/224 |
| 5,084,446 | 1/1992 | Baldoni et al. | 514/53 |
| 5,084,466 | 1/1992 | Alig et al. | 514/353 |
| 5,227,490 | 7/1993 | Hartman et al. | 514/317 |
| 5,254,573 | 10/1993 | Bovy et al. | 514/357 |
| 5,264,420 | 11/1993 | Duggan et al. | 514/19 |
| 5,272,162 | 12/1993 | Tjoeng et al. | 514/344 |
| 5,276,049 | 1/1994 | Himmelsbach et al. | 514/392 |
| 5,281,585 | 1/1994 | Duggan et al. | 514/79 |

FOREIGN PATENT DOCUMENTS

| | | |
|---|---|---|
| 74101 | 10/1991 | Australia. |
| 10403 | 7/1992 | Australia. |
| 20569 | 1/1993 | Australia. |
| 21119 | 2/1993 | Australia. |
| 20892 | 3/1993 | Australia. |
| 27062 | 4/1993 | Australia. |
| 41201 | 12/1993 | Australia. |
| 2008116 | 9/1990 | Canada. |
| 2037153 | 9/1991 | Canada. |
| 2061661 | 9/1992 | Canada. |
| 2094773 | 10/1993 | Canada. |
| 2093770 | 10/1993 | Canada. |
| 0007648 | 6/1980 | European Pat. Off.. |
| 0116729 | 8/1984 | European Pat. Off.. |
| 0136745 | 10/1985 | European Pat. Off.. |
| 0475506 | 3/1992 | European Pat. Off.. |
| 0478362 | 4/1992 | European Pat. Off.. |
| 0478363 | 4/1992 | European Pat. Off.. |
| 0479481 | 4/1992 | European Pat. Off.. |
| 0478328 | 4/1992 | European Pat. Off.. |
| 0513675 | 11/1992 | European Pat. Off.. |
| 0512829 | 11/1992 | European Pat. Off.. |
| 0512831 | 11/1992 | European Pat. Off.. |
| 0529858 | 3/1993 | European Pat. Off.. |
| 0539343 | 4/1993 | European Pat. Off.. |
| 0540334 | 5/1993 | European Pat. Off.. |
| 0560730 | 9/1993 | European Pat. Off.. |
| 05562 | 5/1991 | WIPO. |
| 13552 | 8/1992 | WIPO. |
| 17196 | 10/1992 | WIPO. |
| 18117 | 10/1992 | WIPO. |
| 07867 | 4/1993 | WIPO. |
| 08174 | 4/1993 | WIPO. |
| 08181 | 4/1993 | WIPO. |
| 10091 | 5/1993 | WIPO. |
| 12074 | 6/1993 | WIPO. |
| 14077 | 7/1993 | WIPO. |
| 16038 | 8/1993 | WIPO. |
| 19046 | 9/1993 | WIPO. |
| 22303 | 11/1993 | WIPO. |
| 01396 | 1/1994 | WIPO. |

OTHER PUBLICATIONS

Alig, et al., "Low Molecular Weight, Non–peptide Fibrinogen Receptor Antagonists", J. Med. Chem., 1992, 35, 4393–4407.

Hartman, et al., "Non–peptide Fibrinogen Receptor Antagonists 1. Discovery and Design of Exosite Inhibitors", J. Med. Chem., 1992, 35, 4640–4642.

*Primary Examiner*—Samuel A. Acquah
*Attorney, Agent, or Firm*—Cushman Darby & Cushman

[57] ABSTRACT

The invention concerns allophanic acid derivatives of formula I $$R^1-N(R^2)CO-N(R^3)CO-X^1-Q-X^2-G \qquad I$$

and pharmaceutically acceptable metabolically labile esters or amides thereof, and pharmaceutically acceptable salts thereof, in which $R^1$, $R^2$, $R^3$, $X^1$, Q $X^2$ and G have the meanings given in the specification. The invention also concerns processes for the preparation of the allophanic acid derivatives of formula I, pharmaceutical compositions containing them and their use as inhibitors of the binding of fibrinogen to glycoprotein IIb/IIIa.

12 Claims, No Drawings

ALLOPHANIC ACID DERIVATIVES

This is a divisional of application Ser. No. 08/365,761 filed Dec. 29, 1994 which is a continuation of application Ser. No. 08/266,454 filed Jun. 27, 1994 (now abandoned).

The present invention relates to a group of chemical compounds which inhibit cell adhesion (for example platelet aggregation), to processes for their preparation and to pharmaceutical compositions containing them.

A variety of diseases involve cell adhesion during their development. For example, platelet aggregation is involved in the formation of blood thrombi, which can lead to diseases such as thrombosis, (for example stroke and thrombotic events accompanying unstable angina and transient ischaemic attack), myocardial infarction, atherosclerosis, thromboembolism and reocclusion during and after thrombolytic therapy.

It is widely believed that the platelet membrane glycoprotein IIb–IIIa (GPIIb–IIIa) mediates platelet aggregation. Adhesion molecules such as fibrinogen and von Willebrand Factor are believed to bind to GPIIb–IIIa sites on adjacent platelets and thereby cause them to aggregate. Other adhesion molecules which are known to bind to GPIIb–IIIa are fibronectin, vitronectin and thrombospondin.

Compounds which inhibit platelet aggregation and the binding of adhesion molecules to GPIIb–IIIa are known, for example from U.S. Pat. Nos. 5,039,805 and 5,084,446, Canadian patent applications numbers 2,008,161, 2,037,153 and 2,061,661, and Alig et al., J. Med. Chem., 1992, 35, 4393–4407. Commonly the structures of these compounds are based upon the binding regions of the adhesion molecules, which are peptides. For example, a portion of fibrinogen which is believed to bind to GPIIb–IIIa is the amino acid sequence RGD (arginyl glycyl aspartate).

The ability to inhibit platelet aggregation and to inhibit the binding of fibrinogen to GPIIb–IIIa has now been found to be possessed by certain acid derivatives containing an allophanoyl group.

According to one aspect, therefore, the present invention provides a compound of the general formula I (formula set out at the end of the description together with the other formulae referred to herein by Roman numerals) wherein $R^1$ represents a group of formula II or III in which A is attached meta or para to the position where the group $NR^2CONR^3CO$ is attached and is selected from aminomethyl, guanidino and $R^a N=C(NH_2)-$ where $R^a$ is hydrogen or phenyl which is unsubstituted or substituted by 1 or 2 of halogeno, (1–4C)alkyl, (1–4C)alkoxy, cyano and nitro, E is CH or N, $Z^1$ is hydrogen, halogeno, (1–4C)alkyl, (1–4C)alkoxy, cyano or nitro, T is N or CH, and $X^3$ is a bond, (1–4C)alkylene or, when T is CH, oxy(1–3C)alkylene;

$R^2$ and $R^3$ which may be the same or different, represent hydrogen, (1–4C)alkyl or ar(1–4C)alkyl;

$X^1$ is a bond or (1–4C)alkylene;

Q is a group of formula IV or V in which $Z^2$ is hydrogen, halogeno, (1–4C)alkyl, (1–4C)alkoxy, cyano or nitro, and $Z^3$ is a group of formula $X^2$—$G^a$ in which $X^2$ can have any of the values given hereinafter for $X^2$ and $G^a$ can have any of the values given hereinafter for G, or $G^a$ has any of the values given hereinbefore for $Z^2$;

$X^2$ is a bond, (1–4C)alkylene, oxy(1–3C)alkylene or a group of formula $CH_2CH(NHXR^4)$ in which X is $SO_2$, CO or $CO_2$ and $R^4$ is (1–6C)alkyl, (6–12C)aryl or (6–12C)aryl(1–4C)alkyl, in any of which the aryl group may optionally be substituted by (1–4C)alkyl; and G is a carboxy group or a pharmaceutically acceptable metabolically labile ester or amide thereof; and pharmaceutically acceptable salts thereof.

It will be appreciated that depending on the nature of the substituents, in containing one or more chiral centres, the formula I compounds may exist in and be isolated in one or more different enantiomeric or racemic forms (or a mixture thereof). It is to be understood that the invention includes any of such forms which possesses the property of inhibiting platelet aggregation and inhibiting the binding of fibrinogen to GpIIb–IIIa, it being well known how to prepare individual enantiomeric forms, for example, by synthesis from appropriate chiral starting materials or by resolution of a racemic form. Similarly, the biological properties of a particular form may be readily evaluated, for example by use of one or more of the standard in vitro or ex vivo screening tests detailed hereinbelow.

It will also be appreciated that compounds of formula I wherein $R^1$ represents a group of formula II and A represents the group $R^a N=C(NH_2)-$ may exist in tautomeric forms, and that the invention includes the compounds in any of their tautomeric forms.

A is preferably a group of formula $R^a N=C(NH_2)-$. It is preferably attached para to the position where the group $NR^2CONR^3CO$ is attached.

Examples of values for Ra include hydrogen and phenyl. Examples of substituents on $R^a$ when it is phenyl include fluoro, chloro, bromo, methyl, ethyl, methoxy, ethoxy, cyano and nitro.

When $R^1$ represents a group of formula II bearing the substituent $Z^1$, $Z^1$ may represent, for example hydrogen fluoro, chloro, bromo, methyl, ethyl, methoxy, ethoxy, cyano or nitro.

When $R^1$ represents a group of formula III examples of values for $X^3$ include a bond, methylene, ethylene, trimethylene and, when T is CH, oxymethylene.

Examples of values for $R^1$ include 3-aminomethylphenyl, 4-aminomethylphenyl, 4-amidinophenyl, 4-($N^2$-phenyl)amidinophenyl, 6-amidinopyrid-3-yl, 5-amidinopyrid-2-yl, piperidin-4-yl, piperidin-4-ylmethyl, 2-piperidin-4-ylethyl, piperidin-4-yloxymethyl and piperazin-1-yl.

A (1–4C)alkyl group represented by $R^2$ or $R^3$ may be, for example, methyl or ethyl. An ar(1–4C)alkyl may be, for example, benzyl. Preferably one of $R^2$ and $R^3$ is hydrogen and the other is hydrogen, methyl or benzyl. More preferably each of $R^2$ and $R^3$ represents hydrogen.

Examples of values for $X^1$ when it represents (1–4C)alkylene are methylene and ethylene. Preferably $X^1$ represents a bond.

In the group Q, when it is a group of formula IV, examples of values for $Z^2$ include hydrogen, fluoro, chloro, bromo, methyl, ethyl, methoxy, ethoxy, cyano and nitro. Hydrogen is a preferred value for $Z^2$.

In the group Q, when it is a group of formula IV or V, and $Z^3$ is a group of formula $X^2$—$G^1$, examples of values for $X^2$ include a bond, methylene, ethylene, oxymethylene and groups of formula $CH_2CH(NHXR^4)$ in which X is $SO_2$, CO or $CO_2$ and $R^4$ is methyl, ethyl, propyl, butyl, pentyl, phenyl, tolyl or benzyl, and examples of values for $G^a$ include carboxy (or a pharmaceutically acceptable metabolically labile ester or amide thereof), hydrogen, fluoro, chloro, bromo, methyl, ethyl, methoxy, ethoxy, cyano and nitro. Preferably $Z^3$ is hydrogen or a group of formula $X^2$-$G^a$ in which $X^2$ is oxymethylene and $G^a$ is carboxy.

Examples of values for $X^2$ include a bond, methylene, ethylene, oxymethylene, oxyethylene and groups of formula $CH_2CH(NHXR^4)$ in which X is $SO_2$, CO or $CO_2$ and $R^4$ is methyl, ethyl, propyl, butyl, pentyl, phenyl, tolyl or benzyl. Preferably $X^2$ is oxymethylene or a group of formula $CH_2CH(NHSO_2(CH_2)_3CH_3)$.

Examples of ester derivatives of a carboxy group represented by G include esters formed with alcohols such as (1–6C)alkanols, for example methanol, ethanol, propanol and t-butanol; indanol; benzyl alcohol; adamantol; (1–6C)alkanoyloxy(1–4C)alkanols such as pivaloyloxymethanol; glycolamides; (5-methyl-2-oxo-1,3-dioxol-4-yl)methyl alcohol; and (1–4C)alkoxycarbonyl(1–4C)alkanols.

Examples of amide derivatives of a carboxy group represented by G include amides derived from amines such as (1–4C)alkylamines, for example methylamine; di(1–4C)alkylamines, for example dimethylamine; (1–4C)alkoxy(1–4C)alkylamines such as methoxyethylamine; and amino acids such as glycine or an ester thereof.

Preferably G represents a carboxy group or a (1–4C)alkoxycarbonyl group such as methoxycarbonyl, ethoxycarbonyl or t-butoxycarbonyl.

Particular pharmaceutically acceptable salts include, for example, salts with acids affording physiologically acceptable anions, such as salts with mineral acids, for example a hydrogen halide (such as hydrogen chloride and hydrogen bromide), sulphuric acid or phosphoric acid, and salts with organic acids, for example acetic acid and trifluoroacetic acid. Other pharmaceutically acceptable salts include, for example salts with inorganic bases such as alkali metal and alkaline earth metal salts (for example sodium salts), ammonium salts, and salts with organic amines and quaternary bases forming physiologically acceptable cations such as salts with methylamine, dimethylamine, trimethylamine, ethylenediamine, piperidine, morpholine, pyrrolidine, piperazine, ethanolamine, triethanolamine, N-methylglucamine, tetramethylammonium hydroxide and benzyltrimethylammonium hydroxide.

Particular compounds of the invention include, for example, allophanic acid derivatives of formula I, or pharmaceutically acceptable salts thereof, in which, unless otherwise stated, each of the variable groups $R^1$, $R^2$, $R^3$, $X^1$, Q, $X^2$ and G have any of the meanings defined hereinbefore or in this section concerning particular compounds of the invention:

(a) $R^1$ represents a group of formula II in which A is attached para to the position where the group $NR^2CONR^3CO$ is attached and is selected from aminomethyl, guanidino and $R^aN=C(NH_2)$— where $R^a$ is hydrogen or phenyl, g is CH or N, and $Z^1$ is hydrogen, fluoro, chloro, methyl, methoxy or cyano;

(b) $R^1$ represents a group of formula III in which T is CH or N, and $X^3$ is a bond, methylene, ethylene, trimethylene or, when T is CH, oxymethylene;

(c) $R^2$ and $R^3$ which may be the same or different, represent hydrogen, methyl, ethyl or benzyl;

(d) $X^1$ is a bond or methylene;

(e) Q is a group of formula IV in which $Z^2$ is hydrogen, fluoro, chloro, methyl, methoxy or cyano, and $Z^3$ is hydrogen or a group of formula $X^2$—$G^a$ in which $X^2$ is methylene, ethylene or oxymethylene and $G^a$ is a carboxy group or a pharmaceutically acceptable metabolically labile ester thereof;

(f) Q is a group of formula V in which $Z^3$ is hydrogen or a group of formula $X^2$—$G^a$ in which $X^2$ is methylene, ethylene or oxymethylene and $G^a$ is a carboxy group or a pharmaceutically acceptable metabolically labile ester thereof;

(g) $X^2$ is methylene, ethylene or oxymethylene; and (h) G is a carboxy group or a pharmaceutically acceptable metabolically labile ester thereof.

A preferred compound of the invention is an allophanic acid derivative of formula I wherein $R^1$ represents a group of formula II in which A is attached para to the position where the group $NR^2CONR^3CO$ is attached and is selected from aminomethyl and a group of formula $R^aN=C(NH_2)$— where $R^a$ is hydrogen or phenyl, E is CH and $Z^1$ is hydrogen, fluoro, chloro, methyl or methoxy;

$R^2$ is hydrogen, methyl or benzyl;

$R^3$ is hydrogen, methyl or benzyl;

$X^1$ is a bond;

Q is a group of formula IV in which $Z^2$ is hydrogen, fluoro, chloro, methyl or methoxy, and $Z^3$ is hydrogen or a group of formula $X^2$—$G^a$ in which $X^2$ is oxymethylene and $G^a$ is carboxy, methoxycarbonyl or ethoxycarbonyl;

$X^2$ is oxymethylene; and

G is carboxy, methoxycarbonyl, ethoxycarbonyl, propoxycarbonyl or t-butoxycarbonyl;

or a pharmaceutically acceptable salt thereof.

A further preferred compound of the invention is an allophanic acid derivative of formula I wherein $R^1$ represents a group of formula III in which T is CH or N, and $X^3$ is a bond, methylene, ethylene or, when T is CH, oxymethylene;

$R^2$ is hydrogen, methyl or benzyl;

$R^3$ is hydrogen, methyl or benzyl;

$X^1$ is a bond;

Q is a group of formula IV in which $Z^2$ is hydrogen, fluoro, chloro, methyl or methoxy, and $Z^3$ is hydrogen or a group of formula X2—$G^a$ in which $X^2$ is oxymethylene and $G^a$ is carboxy, methoxycarbonyl or ethoxycarbonyl;

$X^2$ is oxymethylene; and

G is carboxy, methoxycarbonyl, ethoxycarbonyl, propoxycarbonyl or t-butoxycarbonyl;

or a pharmaceutically acceptable salt thereof.

A further preferred compound of the invention is an allophanic acid derivative of formula I wherein $R^1$ represents a group of formula II in which A is attached para to the position where the group $NR^2CONR^3CO$ is attached and is a group of formula $R^aN=C(NH_2)$— where $R^a$ is hydrogen, E is CH and $Z^1$ is hydrogen;

$R^2$ is hydrogen;

$R^3$ is hydrogen or methyl;

$X^1$ is a bond;

Q is a group of formula IV in which $Z^2$ is hydrogen and $Z^3$ is hydrogen or a group of formula X2—$G^a$ in which $X^2$ is oxymethylene and $G^a$ is carboxy;

$X^2$ is oxymethylene; and

G is carboxy, methoxycarbonyl, ethoxycarbonyl or t-butoxycarbonyl; or a pharmaceutically acceptable salt thereof.

A further preferred compound of the invention is an allophanic acid derivative of formula I wherein $R^1$ represents a group of formula III in which T is CH and $X^3$ is ethylene;

$R^2$ is hydrogen;

$R^3$ is hydrogen or methyl;

$X^1$ is a bond;

Q is a group of formula IV in which $Z^2$ is hydrogen and $Z^3$ is hydrogen or a group of formula $X^2—G^a$ in which $X^2$ is oxymethylene and $G^a$ is carboxy;

$X^2$ is oxymethylene; and

G is carboxy, methoxycarbonyl, ethoxycarbonyl or t-butoxycarbonyl;

or a pharmaceutically acceptable salt thereof.

Specific especially preferred compounds of the invention include allophanic acid derivative of formula I selected from: methyl 4-[4-(4-amidinophenyl)allophanoyl]phenoxyacetate and 4-[4-(4-amidinophenyl)allophanoyl]phenoxyacetic acid; or a pharmaceutically acceptable salt thereof.

The compounds of formula I, the metabolically labile esters and amides thereof, and the pharmaceutically acceptable salts thereof may be prepared by procedures analogous to procedures known in the art for the preparation of structurally analogous compounds. Such procedures are included as a further feature of the invention and include the following preferred procedures for the manufacture of a compound of the formula I in which $R^1$, $R^2$, $R^3$, $X^1$, Q, $X^2$ and G have any of the meanings defined above:

(A) For a compound of formula I in which G is carboxy, deprotecting a compound of formula VI in which $G^1$ is a carboxy protecting group.

$G^1$ may be any conventional carboxy protecting group that may be removed without interfering with other parts of the molecule. Examples of carboxy protecting groups include (1–6C)alkyl groups (such as methyl, ethyl, propyl or t-butyl), phenyl and benzyl, the phenyl moiety in any of which may optionally bear 1 or 2 of halogeno, (1–4C)alkyl, (1–4C)alkoxy or nitro.

The deprotection may be carried out using any one or more of the conventional reagents and conditions known in the art for converting carboxylic esters into carboxylic acids. Thus, for example, the deprotection may conveniently be performed by base catalysed hydrolysis, for example by using an alkali metal hydroxide such as lithium, potassium or sodium hydroxide, or a tertiary amine such as triethylamine, in the presence of water. The base catalysed hydrolysis may conveniently be performed in the presence of a solvent such as an alcohol, for example methanol or ethanol, or an ether such as tetrahydrofuran or dioxan. Alternatively the deprotection may be carried out by acid catalysed hydrolysis, for example using acetic acid or trifluoroacetic acid. Suitable solvents for the acid catalysed hydrolysis include alcohols such as those mentioned above, halogenated hydrocarbons such as dichloromethane, ethers such as anisole, and water. The temperature is conveniently in the range of from –10° to 100° C, for example from 10° to 50° C. When the alcohol residue is t-butyl, this may also conveniently be removed by heating, for example at a temperature in the range of from 80° to 150° C., alone or in the presence of a suitable diluent such as diphenyl ether or diphenyl sulphone.

It will be appreciated that a compound of formula I in which G represents carboxy and Q represents a group of formula IV or V wherein $Z^3$ represents a group of formula $X^2—COOH$ may be prepared by this process starting from a compound of formula VI in which Q represents a group of formula IV or V and $Z^3$ represents a group of formula $X^2—COOH$ or $X^2—COOG^1$.

(B) For a compound of formula I in which $R^1$ is a group of formula II and A is an aminomethyl or an amidino group, deprotecting a compound of formula VII in which $A^1$ is a protected aminomethyl or amidino group.

$A^1$ may be any conventional protected aminomethyl or amidino group that may be deprotected without interfering with other parts of the molecule. Examples of protecting groups include oxycarbonyl groups such as t-butoxycarbonyl and benzyloxycarbonyl.

The deprotection may be carried out using any one or more of the conventional reagents and conditions known in the art for removing amine protecting groups. A t-butoxycarbonyl group may be removed by hydrolysis, for example by acid catalysed hydrolysis using an acid such as trifluoroacetic acid. Suitable solvents include halogenated hydrocarbons such as dichloromethane. A benzyloxycarbonyl group may conveniently be removed, for example, by hydrogenation in the presence of a palladium catalyst such as palladium on charcoal. The temperature is conveniently in the range of from –10° to 100° C., for example from 10° to 50° C.

In some cases the reaction conditions required to perform process (A) are the same as those required to perform process (B). In such cases it is possible to perform processes (A) and (B) at the same time by starting with a compound having an appropriate carboxy protecting group and an appropriately protected aminomethyl or amidino group. Such a compound is represented by the formula VIII.

(C) For a compound of formula I in which $R^2$ and $R^3$ represent hydrogen atoms, reacting an isocyanate of formula IX with an amine of formula X.

Suitable solvents include halogenated hydrocarbons such as dichloromethane and nitriles such as acetonitrile. The reaction is conveniently performed at a temperature in the range of from –10° to 100° C.

(D) For a compound of formula I in which $X^2$ is a group of formula $CH_2CH(NHXR^4)$, reacting a compound of formula XI in which $X^{2a}$ is $CH_2CH(NH_2)$, or an acid addition salt thereof, with a compound of formula XII in which $U^1$ is a leaving atom or group.

Examples of values for $U^1$ include halogen such as chlorine or bromine and hydrocarbylsulphonyloxy such as methanesulphonyloxy and p-toluenesulphonyloxy. Examples of acid addition salts include for example, the hydrochloride. The reaction may conveniently be effected at a temperature in the range of from –10° to 120° C. preferably from 10° to 100° C. Suitable solvents include for example ethers such as tetrahydrofuran, amides such as dimethylformamide, nitriles such as acetonitrile, halogenated hydrocarbons such as dichloromethane and alcohols such as ethanol. The reaction is conveniently performed in the presence of a base, for example a tertiary amine such as triethylamine.

(E) For a compound of formula I in which $R^1$ is a group of formula II and A is a group of formula $R^aN=C(NH_2)—$, reacting a compound of formula XIII, in which $U^2$ is a leaving atom or group, with a compound of formula $R^aNH_2$, or an acid addition salt thereof.

Examples of values for $U^2$ include (1–4C)alkylthio groups such as methylthio. Suitable media for the reaction include alcohols such as methanol or ethanol, and halogenated hydrocarbons such as dichloromethane. The reaction is conveniently performed at a temperature in the range of from –10° to 100° C. An acid addition salt of a compound of formula $R^aNH_2$ may be for example an addition salt of an organic acid such as acetic acid or an inorganic acid such as hydrochloric acid.

The intermediates used in the aforementioned processes are either known or may be prepared by methods analogous to methods known for preparing known compounds. In general, the intermediates containing an acylureido group may be prepared by reacting the appropriate isocyanate derivative with the appropriate amine.

Thus, the compounds of formula VI in which $R^2$ and $R^3$ represent hydrogen may be prepared by reacting an isocyanate of formula XIV with an amine of formula X by a method analogous to that of process (C) described hereinabove.

The compounds of formula VI in which $R^1$ is a group of the formula II and A is an aminomethyl group may also be prepared by selectively deprotecting a compound of formula VIII. Similarily, the compounds of formula VII may also be prepared by selectively deprotecting a compound of formula VIII.

The compounds of formula VIII in which $R^2$ and $R^3$ represent hydrogen may be prepared by reacting an amine of formula XV with an isocyanate of formula XIV following a method analogous to that of process (C) described hereinabove.

The compounds of formula IX and XIV may be prepared respectively by reacting a compound of formula XVI or XVII, or a protected derivative thereof, with oxalyl chloride. The reaction is conveniently effected at a temperature in the range of from −10° to 100° C. Suitable solvents include halogenated hydrocarbons such as dichloromethane and nitriles such as acetonitrile.

The compounds of formula XI in which $R^2$ and $R^3$ are hydrogen may be prepared by a method analogous to process (C), by reacting an amine of formula X with an isocyanate of formula XVIII, or a protected derivative thereof, followed if necessary by the removal of the protecting group(s).

The compounds of formula XIII in which $U^2$ is a (1–4C)alkylthio group may be prepared by reacting a compound of formula XIX with an alkylating agent, for example a (1–4C)alkyl halide such as methyl iodide. Suitable media for the reaction include ketones such as acetone. Conveniently the reaction may be performed at a temperature in the range of from 0° to 100° C.

The compounds of formula XIX may be prepared by reacting a compound of formula XX with hydrogen sulphide. The reaction is conveniently effected in the presence of a base such as triethylamine and in the presence of a solvent such as pyridine.

The compounds of formula XX may be prepared by reacting an amine of formula XXI with an isocyanate of formula IX. Suitable solvents for the reaction include nitriles such as acetonitrile.

The compounds of formula XVIII may be prepared by reacting a compound of formula XXII, or a protected derivative thereof, with oxalyl chloride. Suitable solvents include halogenated hydrocarbons such as 1,2-dichloroethane.

The compounds of formula I may be converted into pharmaceutically acceptable salts and/or metabolically labile esters or amides thereof by methods well known in the art. For example, a pharmaceutically acceptable salt may be formed by reacting a compound of formula I with an acid capable of affording a physiologically acceptable anion, or a base capable of affording a physiologically acceptable cation. A pharmaceutically acceptable metabolically labile ester or amide may be formed respectively by esterifying a compound of formula I using a conventional technique, or by reacting an acid, or a reactive derivative thereof, with an appropriate amine. Similarly, when an optically active form of a chiral compound of formula I is required, either one of processes (A)–(E) above may be carried out using the appropriate optically active starting material or else a racemic form may be resolved by a conventional procedure, for example, using an optically active form of a suitable acid.

A suitable reactive derivative of an acid may be, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol or an alcohol such as 1-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide.

Many of the intermediates, for example compounds of formulae VI, VII, VIII, XI, XIII, XIX and XX are novel and form further aspects of this invention.

The ability of the compounds of formula I to inhibit platelet aggregation may be demonstrated using a standard test (a) based on that described by Born (*Nature*, 1962, 194, 927–929) and involving:

(i) aggregating human, citrated, platelet-rich plasma by addition of adenosine diphosphate (ADP) so as to generate a dose-response curve;

(ii) generating a dose-response curve for ADP stimulated platelet aggregation in the presence of increasing amounts of a test compound (generally in the range $10^{-5}$M to $10^{-10}$M); and (iii) calculating a $pA_2$ value indicating potency of platelet aggregation inhibition for the test compound, averaged over several concentrations, from the calculated 50% response value for ADP aggregation in the presence and absence of the test compound.

Test (a) may be modified so as to assess the effects of a test compound ex vivo on the aggregation of human blood platelets after administration of the test compound to a laboratory animal, such as a rat, rabbit, guinea pig, mouse or dog. For example, groups of four male, fasted Alderley Park Wistar rats are orally dosed with a test compound or appropriate vehicle, and at suitable time intervals (1, 3, 5 and 8 hours after dosing) animals are anaesthetised with fluothane and bled by heart puncture. Blood is collected into 3.2% citrate (1 part to 9 parts whole blood) and platelet poor plasma (ppp) prepared by centrifugation (4500×g for 10 minutes).

Human blood is collected into 3.2% trisodium citrate (1 part to 9 parts whole blood) and centrifuged (200×g for 15 minutes) to produce platelet rich plasma (prp).

Equal volumes (125 µl) of rat ppp and human prp are mixed together, ADP added, and the whole incubated (37° C.) and stirred (900 rpm) in a BioData platelet aggregometer. Aggregation is induced with ADP and agonist $EC_{50}$ values calculated for human prp/rat ppp mixtures from animals dosed with test compound or vehicle. A mean concentration ratio (concentration of ADP required to cause a 50% aggregation response in human prp/rat ppp mixtures from animals dosed with antagonist, divided by the concentration of ADP to cause 50% aggregation in human prp/rat ppp mixtures from animals dosed with vehicle) is calculated at each time point.

The ability of the compounds of formula I to inhibit binding of fibrinogen to GPIIb–IIIa may be demonstrated using the following standard test (b) involving:

(i) Preparation of human platelet lysates

Platelet rich plasma (prp) is harvested by centrifugation (1000 rpm, 15 minutes) of whole blood anticoagulated with acid citrate dextrose (trisodium citrate 85 mM, citric acid 70 mM, d-glucose 110 mM) 1 part to 6 parts blood. Prostacyclin ($PGI_2$, 1 μM) is added to the prp before centrifugation (2400 rpm, 15 min) and the resulting pellet is resuspended in modified Tyrodes' solution (NaCl 130 mM, KCl 26 mM, $NaHCO_3$, 12 mM, $NaH_2PO_4$ 0.5 mM, $MgCl_2$ 1 mM, $CaCl_2$ 20 mM, Glucose 12 mM, HEPES 5 mM) containing bovine serum albumin 3.5 g/L, $PGI_2$ 1 μM and hirudin 0.5 U/ml. The platelet suspension is centrifuged (2400 rpm, 15 minutes) and the resultant pellet resuspended in 500 μl of lysis buffer (octyl glucoside 50 mM, HEPES 10 mM, NaCl 150 mM, $CaCl_2$ 1 mM, $MgCl_2$ 1 mM, PMSF 1 mM, NEM 10 mM, leupeptin 0.1 mM), agitated at 4° C. for 15 minutes then centrifuged at 24000 rpm, 15 minutes. The supernatant is stored at 4° C. and the pellet re-suspended in 500 μl of lysis buffer. The centrifugation process is repeated a further 3 times, the pooled supernatants being stored at −70° C.

(ii) Receptor purification

Glycoprotein IIb/IIIa is isolated from human platelet lysates using a 2 ml peptide (KYGRGDS) coupled CNBr activated Sepharose affinity column. A 1.5 ml volume of platelet lysate is placed on the column and allowed to stand overnight at 4° C. Buffer (30 ml, octyl glucoside 25 mM, HEPES 10 mM, NaCl 150 mM, $CaCl_2$ 1 mM, $MgCl_2$ 1 mM, PMSF 1 mM, NEM 10 mM, leupeptin 0.1 mM) is passed through the column and 2 ml fractions are collected throughout. GPIIb/IIIa is eluted with 12 ml of buffer containing HHLGGAKQAGDV (2mg/ml, pH 7.5), the column is washed using 4 ml buffer and the remaining GPIIb/IIIa eluted using 12 ml buffer containing GRGDSPG (1 mg/ml pH 7.5). The column is finally washed using 20 ml of buffer and can be used for up to three such preparations. Fractions containing GPIIb/IIIa are identified using gel electrophoresis and immunoblotting, pooled and stored at −70° C.

(iii) GPIIb/IIIa ELISA 96 well microtitre plates are coated with 100 μl purified human platelet fibrinogen receptor (GPIIb/IIIa) diluted in coating buffer (Tris-HCl 20 mM, NaCl 150 mM, $CaCl_2$ 1 mM, pH 7.4) and left overnight at 4° C. The plates are washed using washing buffer (Tris-HCl 50 mM, NaCl 100 mM, $CaCl_2$ 2 mM, pH 7.4) and non-specific binding blocked by the addition of 200μl 2% BSA (2 hours, 30° C.). The plates are washed prior to incubation (2 hours, 30° C.) with 100 μl biotinylated fibrinogen (10 nM) containing either vehicle or test compound. The plates are washed, incubated with streptavidin (5 μg/ml, 1 hour, ambient temperature), then washed again before the addition of 100 μl biotinylated horse radish peroxidase (0.1 μg/ml, 1 hour, ambient temperature). The plates are then washed and equal volumes of peroxidase substrate (3,3',5,5'-tetramethylbenzidine 0.4 g/l) and $H_2O_2$ (0.02%) are mixed together immediately before addition of 150 μl to each well. Colour is allowed to develop for 10–15 minutes before optical densities are read at 650 nm.

---

Abbreviations

| | |
|---|---|
| PMSF | Phenylmethylsulphonyl fluoride |
| HEPES | 2-[4-(2-hydroxyethyl)piperazin-1-yl]ethanesulphonic acid |
| NEM | N-ethylmaleimide |

The concentration of compound required to cause 50% inhibition of biotinylated fibrinogen binding is calculated and expressed as a $pIC_{50}$ ($-\log(IC_{50})$).

The compounds of formula I exemplified herein have been found to show effects in the following ranges in at least one of the above tests:

test (a): $pA_2$ of >4.5
test (b): $pIC_{50}$ of >4.5

In general, it has been found that compounds of formula I in which G is carboxy show a higher level of activity in test (a) and test (b) than those in which G is an ester group.

For example, the compound described in Example 1 hereinafter has been found to give a $pA_2$ of 7.5 in test (a) and a $pIC_{50}$ of 6.9 in test (b), whereas the compound of Example 2 has been found to give a $pA_2$ of 7.6 in test (a) and a $pIC_{50}$ of 7.6 in test (b).

As stated previously, the compounds of formula I may be used in the therapy or prevention of diseases in which cell adhesion (especially platelet aggregation) is involved, for example venous or arterial thrombosis (for example pulmonary embolism, stroke and thrombotic events accompanying unstable angina and transient ischaemic attack), myocardial infarction, migraine, atherosclerosis, thromboembolism and reocclusion during and after thrombolytic therapy. The compounds may also be useful for the prevention of reocclusion or restenosis following percutaneous transluminal coronary angioplasty (PTCA) and coronary artery bypass graft. It will also be appreciated that the compounds may be useful in the treatment of other diseases mediated by binding of adhesion molecules to GPIIb/IIIa, for example cancer.

According to another aspect, therefore, the invention provides a method of inhibiting platelet aggregation in a warm-blooded mammal requiring such treatment, which comprises administering an effective amount of a compound of formula I, or a pharmaceutically acceptable metabolically labile ester or amide thereof, or a pharmaceutically acceptable salt thereof.

According to yet another aspect, the invention provides a method of inhibiting binding of fibrinogen to GPIIb/IIIa in a warm-blooded animal requiring such treatment, which comprises administering an effective amount of a compound of formula I, or a pharmaceutically acceptable metabolically labile ester or amide thereof, or a pharmaceutically acceptable salt thereof.

According to a further aspect, the invention provides the use of a compound of formula I, or a pharmaceutically acceptable metabolically labile ester or amide thereof, or a pharmaceutically acceptable salt thereof, for the manufacture of a medicament for the prevention or treatment of a disease involving platelet aggregation.

According to yet another aspect, the invention provides the use of a compound of formula I, or a pharmaceutically acceptable metabolically labile ester or amide thereof, or a pharmaceutically acceptable salt thereof, for the manufacture of a medicament for the prevention or treatment of a disease involving binding of fibrinogen to GPIIb/IIIa.

In general, a compound of formula I will be administered for this purpose by an oral, rectal, topical, intravenous, subcutaneous, intramuscular or inhalation route, so that a dose in the range of from 0.01 to 50 mg/kg body weight will be given, depending upon the route of administration, the age and sex of the patient, and the severity of the condition to be treated.

The compounds of formula I will generally be used in the form of a pharmaceutical composition comprising a compound of formula I, or a pharmaceutically acceptable metabolically labile ester or amide thereof, or a pharmaceutically acceptable salt thereof, together with a pharmaceutically acceptable diluent or carrier. Such a composition is provided as a further feature of the invention and may be in a variety of dosage forms. For example, it may be in the form of tablets, capsules, solutions or suspensions for oral administration; in the form of creams or ointments or a transdermal (skin) patch for topical administration; in the form of a suppository for rectal administration; in the form of a sterile solution or suspension for administration by intravenous or intramuscular injection; in the form of an aerosol or a nebuliser solution or suspension, for administration by inhalation; and in the form of a powder, together with pharmaceutically acceptable inert solid diluents such as lactose, for administration by insufflation. Depending upon the route of administration, the composition will, in general, comprise, for example, 1 to 99% by weight of a compound of formula I.

The pharmaceutical compositions may be obtained by conventional procedures using pharmaceutically acceptable diluents and carriers well known in the art. Tablets and capsules for oral administration may conveniently be formed with an enteric coating, for example comprising cellulose acetate phthalate, to minimise contact of the active ingredient of formula I with stomach acids.

The compounds according to the invention may be co-adminstrated or co-formulated with one or more agents known to be of value in diseases or conditions intended to be treated; for example a known platelet aggregation inhibitor (e.g. aspirin, a thromboxane antagonist or a thromboxane synthase inhibitor), hypolipidemic agent, anti-hypertensive agent, thrombolytic agent (such as streptokinase, urokinase, prourokinase, tissue plasminogen activator and derivatives thereof), beta-adrenergic blocker or a vasodilator may usefully also be present in a pharmaceutical composition of the invention for use in treating a heart or vascular disease or condition.

In addition to their use in therapeutic medicine, the compounds of formula I are also useful as pharmacological tools in the development and standardisation of test systems for the evaluation of the effects of adhesion molecules in laboratory animals such as cats, dogs, rabbits, monkeys, rats and mice, as part of the search for new therapeutic agents. The compounds of formula I may also be used because of their platelet aggregation inhibitory properties in helping to store blood and to maintain the viability of blood and blood vessels in warm-blooded animals (or parts thereof) undergoing artificial extracorporeal circulation, for example during limb or organ transplants. When used for this purpose a compound of formula I, or a pharmaceutically acceptable salt thereof, will generally be administered so that a steady state concentration in the range, for example, 0.1 to 10 mg per liter is achieved in the blood.

The invention will now be illustrated by the following nonlimiting Examples in which unless otherwise stated:(i)

(i) concentrations and evaporations were carried out by rotary evaporation in vacuo;

(ii) operations were carried out at ambient temperature, that is, in the range 18°–26° C.;

(iii) column chromatography was carried out on silica (Merck Art. 9385) available from E Merck and Co., Darmstadt, Germany;

(iv) yields are given for illustration only and are not necessarily the maximum attainable by diligent process development;

(v) proton NMR spectra were normally determined at 200 MHz or 250 MHz in dimethylsulphoxide-$d_6$ using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d, doublet; and (vi) ether refers to diethyl ether, DMSO to dimethylsulphoxide and TFA to trifluoroacetic acid.

EXAMPLE 1

Methyl 4-[4-(4-amidinophenyl)allophoyl]phenoxyacetate, acetate salt

Ammonium acetate (1 g) was added to a stirred suspension of methyl 4-[4-(4-methylthiocarbonimidoylphenyl)allophanoyl]phenoxyacetate, hydroiodide salt (340 mg), in methanol (6 ml) and dichloromethane (4 ml). The reaction mixture was stirred at ambient temperature for 3 days and then heated to reflux for 30 hours. The solvents were removed in vacuo and the resultant solid residue was stirred under methanol for 1 hour. The solid was collected and washed with methanol to give the title compound (249 mg) as a white solid; m.p. 225°–229° C. (decomposes); NMR Spectrum (DMSO-$d_6$) 1.75 (3H, s), 3.71 (3H, s), 4.92 (2H, s), 7.07 (2H, d), 7.80 (4H, s), 8.04 (2H, d); Mass Spectrum m/Z 371 (M+H)$^+$; Elemental Analysis: calculated for $C_{18}H_{18}N_4O_5$. 1.0 $CH_3CO_2H$. 0.2 $H_2O$: C, 55.3%; H, 5.2%; N, 12.9%; found: C, 55.4%; H, 5.1%; N, 12.9%.

The necessary starting material was prepared as follows:

(a) To a stirred suspension of 4-methoxycarbonylmethoxybenzamide (preparation described in Bergeson, S. H. et al. (1986) European Patent Application No. 189305 A2) (2.72 g) in 1,2-dichloroethane (50 ml) was added oxalyl chloride (2.2 ml). The reaction mixture was heated to reflux with stirring for 17 hours. The solvents were removed in vacuo and acetonitrile (30 ml) was added to the residue. Insoluble material was removed by filtration and the filtrate was added to a solution of 4-aminobenzonitrile (1.54 g) and triethylamine (6.5 ml) in acetonitrile (100 ml) at ambient temperature. The reaction mixture was stirred for 1 hour and the precipitated solid was collected, washed with acetonitrile and dried to give methyl 4-[4-(4-cyanophenyl)allophanoyl] phenoxyacetate (1.4 g) as a white solid; m.p. 204°–207° C.; NMR Spectrum (DMSO-$d_6$) 3.71 (3H, s), 4.92 (2H, s), 7.08 (2H, d), 7.80 (4H, s), 8.03 (2H, d), 11.01 (1H, s), 11.15 (1H, s); Mass Spectrum m/Z 354 (M+H)$^+$.

(b) A mixture of the product of step (a) (600 mg), pyridine (56 ml) and triethylamine (8 ml) was covered with a blanket of $H_2S$ gas and stirred at ambient temperature overnight. The dark green reaction mixture was evaporated to dryness and the residue was stirred with dry ether for 1 hour. The resultant solid was collected and washed thoroughly with ether to give methyl 4-[4-(4-thiocarbamoylphenyl)allophanoyl] phenoxyacetate (593 mg) as a yellow solid; m.p. 215°–218° C. (decomposes); NHR Spectrum (DMSO-$d_6$+ $CD_3CO_2D$) 3.73 (3H, s), 4.90 (2H, s), 7.08 (2H, d), 7.64 (2H, d), 7.98 (2H, d), 8.06 (2H, d); Mass Spectrum m/Z 388 (M+H)$^+$.

(c) Iodomethane (5 ml) was added to a stirred suspension of the product of step (b) (550 mg) in acetone (50 ml). The reaction mixture was stirred at ambient temperature for 2 days and then filtered. The collected solid was washed with acetone and dried to give methyl 4-[4-(4-methylthiocarbonimidoylphenyl)allophanoyl]phenoxyacetate, hydroiodide salt (550 mg), as a yellow solid; m.p. 216°–219° C. (decomposes); NHR Spectrum (DMSO-$d_6$) 2.82 (3H, s), 3.71 (3H, s), 4.93 (2H, s), 7.09 (2H, d), 7.91 (4H, m), 8.05 (2H, d), 11.08 (1H, s), 11.28 (1H, s).

EXAMPLE 2

4-[4-(4-Amidinophenyl)allophanoyl]phenoxyacetic acid

To a stirred suspension of the product of Example 1 (100 mg) in methanol (25 ml) was added a 1% (by volume)

solution of triethylamine in water (25 ml). The reaction mixture was stirred at ambient temperature for 24 hours and filtered. The collected solid was washed thoroughly with methanol and dried to give the title compound (60 mg) as a cream solid; m.p. 285°–288° C. (decomposes); NMR Spectrum (TFA+DMSO-d$_6$) 4.90 (2H, s), 7.14 (2H, d), 7.90 (8H, m), 8.07 (2H, d); Mass Spectrum m/Z 357 (H+H)$^+$; Elemental Analysis: calculated for $C_{17}H_{16}N_4O_5$: C, 53.5Z; H, 4.97%; N, 14.7; found: C, 53.6%; H, 4.8%; N, 14.6%.

EXAMPLE 3

Illustrative pharmaceutical dosage forms suitable for presenting the compounds of the invention for therapeutic or prophylactic use include the following, which may be obtained by conventional procedures well known in the art.

| | | |
|---|---|---|
| a) | Tablet I | mg/tablet |
| | Active ingredient | 1.0 |
| | Lactose Ph. Eur. | 93.25 |
| | Croscarmellose sodium | 4.0 |
| | Maize starch paste (5% w/v aqueous paste) | 0.75 |
| | Magnesium stearate | 1.0 |
| b) | Tablet II | mg/tablet |
| | Active ingredient | 50 |
| | Lactose | 223.75 |
| | Croscarmellose sodium | 6.0 |
| | Maize starch | 15.0 |
| | Polyvinylpyrrolidone (5% w/v aqueous paste) | 2.25 |
| | Magnesium stearate | 3.0 |
| c) | Tablet III | mg/tablet |
| | Active ingredient | 100 |
| | Lactose | 182.75 |
| | Croscarmellose sodium | 12.0 |
| | Maize starch paste (5% w/v aqueous paste) | 2.25 |
| | Magnesium stearate | 3.0 |
| (d) | Capsule | mg/capsule |
| | Active ingredient | 10 |
| | Lactose Ph. Eur. | 488.5 |
| | Magnesium stearate | 1.5 |
| (e) | Injection | mg/ml |
| | Active ingredient (acid addition salt) | 1.0 |
| | Sodium chloride | 9.0 |
| | Purified water to 1.0 ml | |

CHEMICAL FORMULAE $R^1-N(R^2)CO-N(R^3)CO-X^1-Q-X^2-G$  I

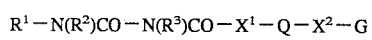 II

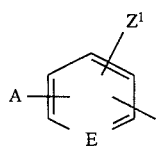 III

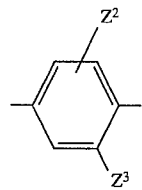 IV

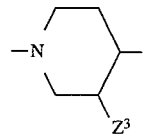 V $R^1-N(R^2)CO-N(R^3)CO-X^1-Q-X^2-COOG^1$  VI

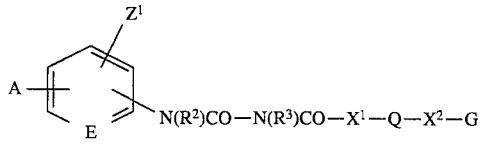 VII

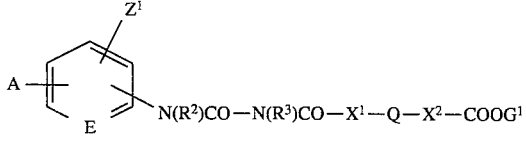 VIII $OCN-CO-X^1-Q-X^2-G$  IX
$R^1-NH_2$  X
$R^1-N(R^2)CO-N(R^3)CO-X^1-Q-X^{2a}-G$  XI
$R^4X-U^1$  XII

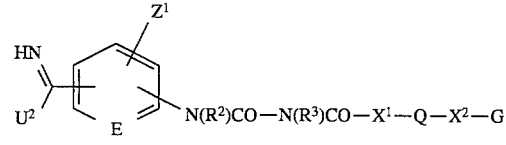 XIII $OCN-CO-X^1-Q-X^2-COOG^1$  XIV

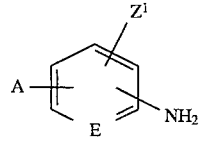 XV $H_2NCO-X^1-Q-X^2-G$  XVI
$H_2NCO-X^1-Q-X^2-COOG^1$  XVII
$OCN-CO-X^1-Q-X^{2a}-G$  XVIII

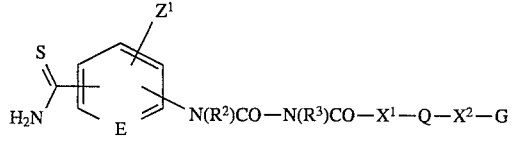 XIX

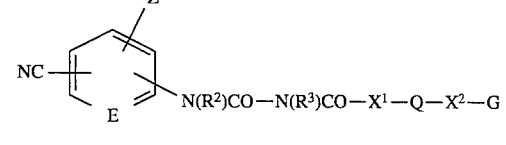 XX

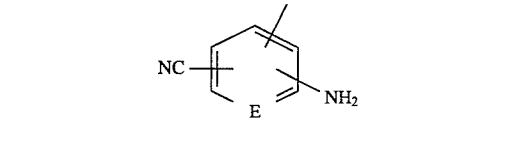 XXI

-continued
CHEMICAL FORMULAE $$H_2NCO-X^1-Q-X^{2a}-G \quad\quad XXII$$

We claim:

1. A pharmaceutical composition comprising an allophanic acid derivative of formula I $$R^1-N(R^2)CO-N(R^3)CO-X^1-Q-X^2-G \quad\quad I$$

wherein $R^1$ represents a group of formula II or III

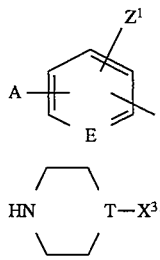

in which A is attached meta or para to the position where the group $NR^2CONR^3CO$ is attached and is selected from aminomethyl, guanidino and $R^aN\!=\!C(NH_2)$— where $R^a$ is hydrogen or phenyl which us unsubstituted or substituted by 1 or 2 of halogeno, (1–4C)alkyl, (1–4c) alkoxy, cyano and nitro, E is CH or N, $Z^1$ is hydrogen, halogeno, (1–4C)alkyl, (1–4C)alkoxy, cyano or nitro, T is N or CH, and $X^3$ is a bond, (1–4C)alkylene or, when T is CH, oxy(1–3C)alkylene;

$R^2$ and $R^3$, which may be the same or different, represent hydrogen, (1–4C)alkyl or ar(1–4c)alkyl;

$X^1$ is a bond or (1–4C) alkylene;

Q is a group of formula Iv or V

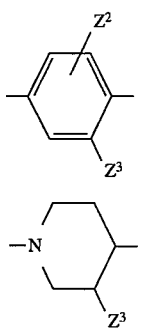

in which $Z^2$ is hydrogen, halogone, (1–4c)alkyl, (1–4C)alkoxy, cyano or nitro, and $Z^3$ is a group of formula $X^2$—$G^a$ in which $X^2$ can have any of the values given hereinafter for $X^2$ and $G^a$ can have any of the values given hereinafter for G, or $G^a$ has any of the values given hereinbefore for $Z^2$;

$X^2$ is a bond, (1–4C)alkylene, oxy(1–3C)alkylene or a group of formula $CH_2CH(NHXR^4)$ in which X is $SO_2$, CO or $CO_2$ and $R^4$ is (1–6C)alkyl, (6–12c)aryl or (6–12C)aryl(1–4C)alkyl, in any of which the aryl group may optionally be substituted by (1–4C)alkyl; and G is a carboxy group or a pharmaceutically acceptable metabolically labile ester or amide thereof; and pharmaceutically acceptable salts thereof, together with a pharmaceutically acceptable diluent or carrier.

2. The pharmaceutical composition of claim 1 wherein $R^1$ represents a group of formula II in which A is attached para to the position where the group $NR^2CONR^3CO$ is attached and is selected from aminomethyl and a group of formula $R^aN\!=\!C(NH_2)$— where $R^a$ is hydrogen or phenyl, E is CH and $Z^1$ is hydrogen, fluoro, chloro, methyl or methoxy;

$R^2$ is hydrogen, methyl or benzyl;

$R^3$ is hydrogen, methyl or benzyl;

$X^1$ is a bond;

Q is a group of formula IV in which $Z^2$ is hydrogen, fluoro, chloro, methyl or methoxy, and $Z^3$ is hydrogen or a group of formula $X^2$—$G^a$ in which $X^2$ is oxymethylene and $G^a$ is carboxy, methoxycarbonyl or ethoxycarbonyl; .

$X^2$ is oxymethylene; and

G is carboxy, methoxycarbonyl, ethoxycarbonyl, propoxycarbonyl or t-butoxycarbonyl;

or a pharmaceutically acceptable salt thereof.

3. The pharmaceutical composition of claim 1 wherein $R^1$ represents a group of formula III in which T is CH or N, and $X^3$ is a bond, methylene, ethylene or, when T is CH, oxymethylene;

$R^2$ is hydrogen, methyl or benzyl;

$R^3$ is hydrogen, methyl or benzyl;

$X^3$ is a bond;

Q is a group of formula Iv in which $Z^2$ is hydrogen, fluoro, chloro, methyl or methoxy, and $Z^3$ is hydrogen or a group of formula $X^2$—$G^a$ in which $X^2$ is oxymethylene and $G^a$ is carboxy, methoxycarbonyl or ethoxycarbonyl;

$X^2$ oxymethylene; and

G is carboxy, methoxycarbonyl, ethoxycarbonyl, propoxycarbonyl or t-butoxycarbonyl;

or a pharmaceutically acceptable salt thereof.

4. The pharmaceutical composition of claim 1 wherein $R^1$ represents a group of formula II in which A is attached para to the position where the group $NR^2CONR^3CO$ is attached and is a group of formula $R^aN\!=\!C(NH_2)$— where $R^a$ is hydrogen, E is CH and $Z^1$ is hydrogen;.

$R^2$ is hydrogen;

$R^3$ is hydrogen or methyl;

$X^1$ is a bond;

Q is a group of formula IV in which $Z^2$ is hydrogen and $Z^3$ is hydrogen or a group or formula $X^2$—$G^a$ in which $X^2$ is oxymethylene and $G^a$ is carboxy;

$X^2$ is oxymethylene; and

G is carboxy, methoxycarbonyl, ethoxycarbonyl or t-butoxycarbonyl;

or a pharmaceutically acceptable salt thereof.

5. The pharmaceutical composition of claim 1 wherein $R^1$ represents a group of formula III in which T is CH and $X^3$ is ethylene;

$R^2$ is hydrogen;

$R^3$ is hydrogen or methyl;

$X^1$ is a bond;

Q is a group of formula IV in which $Z^2$ is hydrogen and $Z^3$ is hydrogen or a group of formula $X^2$—$G^a$ in which $X^2$ is oxymethylene and $G^a$ is carboxy;

$X^2$ is oxymethylene; and

G is carboxy, methoxycarbonyl, ethoxycarbonyl or t-butoxycarbonyl;

or a pharmaceutically acceptable salt thereof.

6. The pharmaceutical composition of claim 1 wherein the allophanic acid derivative of formula I is selected from: methyl 4-[4-(-amidinophenyl)allophanoyl]phenoxyacetate and 4-[4-(-amidinophenyl)allophanoyl]phenoxyacetic acid; or a pharmaceutically acceptable salt thereof.

7. A method of inhibiting platelet aggregation is a warm-blooded mammal requiring such treatment, which comprises administering a platelet aggregation inhibiting effective amount of an allophanic acid derivative of formula I $$R^1—N(R^2)CO—N(R^3)CO—X^1—Q—X^2—G \qquad I$$

wherein $R^1$ represents a group of formula II or III

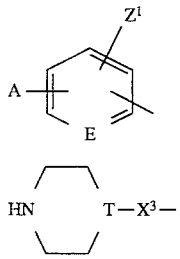

in which A is attached meta or para to the position where the group $NR^2CONR^3CO$ is attached and is selected from aminomethyl, guanidino and $R^aN=C(NH_2)—$ where $R^a$ is hydrogen or phenyl which us unsubstituted or substituted by 1 or 2 of halogeno, (1–4C)alkyl, (1–4c)alkoxy, cyano and nitro, E is CH or N, $Z^1$ is hydrogen, halogeno, (1–4C)alkyl, (1–4C)alkoxy, cyano or nitro, T is N or CH, and $X^3$ is a bond, (1–4C)alkylene or, when T is CH, oxy(1–3C)alkylene;

$R^2$ and $R^3$, which may be the same or different, represent hydrogen, (1–4C)alkyl or ar(1–4C)alkyl;

$X^1$ is a bond or (1–4c)alkylene;

Q is a group of formula IV or V

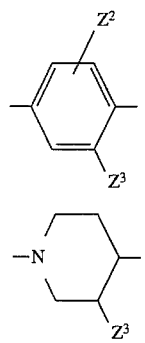

in which $Z^2$ is hydrogen, halogeno, (1–4C)alkyl, (1–4C)alkoxy, cyano or nitro, and $Z^3$ is a group of formula $X^2—G^a$ in which $X^2$ can have any of the values given hereinafter for $X^2$ and $G^a$ can have any of the values given hereinafter for G, or $G^a$ has any of the values given hereinbefore for $Z^2$;

$X^2$ is a bond, (1–4c)alkylene, oxy(1–3C)alkylene or a group of formula $CH_2CH(NHXR^2)$ in which X is $SO_2$, Co or $CO_2$ and $R^4$ is (1–6c)alkyl, (6–12C)aryl or (6–12C)aryl(1–4C)alkyl, in any of which the aryl group may optionally be substituted by (1–4C)alkyl; and G is a carboxy group or a pharmaceutically acceptable metabolically labile ester or amide thereof; and pharmaceutically acceptable salts thereof.

8. The method of claim 7 wherein $R^1$ represents a group of formula II in which A is attached pard to the position where the group $NR^2CONR^3CO$ is attached and is selected from aminomethyl and a group or formula $R^aN=C(NH_2)—$ where $R^a$ is hydrogen or phenyl, E is CH and $Z^1$ is hydrogen, fluoro, chloro, methyl or methoxy;

$R^2$ is hydrogen, methyl or benzyl;

$R^3$ is hydrogen, methyl or benzyl;

$X^1$ is a bond;

Q is a group of formula IV in which $Z^2$ is hydrogen, fluoro, chloro, methyl or methoxy, and $Z^3$ is hydrogen or a group of formula $X^2—G^a$ in which $X^2$ is oxymethylene and $G^a$ is carboxy, methoxycarbonyl or ethoxycarbonyl;

$X^2$ is oxymethylene; and

G is carboxy, methoxycarbonyl, ethoxycarbonyl, propoxycarbonyl or t-butoxycarbonyl;

or e pharmaceutically acceptable salt thereof.

9. The method of claim 7 wherein $R^1$ represents a group of formula III in which T is CH or N, and $X^3$ is a bond, methylene, ethylene or, when T is CH, oxymethylene;

$R^2$ is hydrogen, methyl or benzyl;

$R^3$ is hydrogen, methyl or benzyl;

$X^1$ is a bond;

Q is a group of formula IV in which $Z^2$ is hydrogen, fluoro, chloro, methyl or methoxy, and $Z^3$ is hydrogen or a group of formula $X^2—G^a$ in which $X^2$ is oxymethylene and $G^a$ is carboxy, methoxycarbonyl or ethoxycarbonyl;

$X^2$ is oxymethylene; and

G is carboxy, methoxycarbonyl, ethoxycarbonyl, propoxycarbonyl or t-butoxycarbonyl;

or a pharmaceutically acceptable salt thereof.

10. The method of claim 7 wherein $R^1$ represents a group of formula II in which A is attached pare to the position where the group $NR^2CONR^3CO$ is attached and is a group of formula $R^aN=C(NH_2)—$ where $R^a$ is hydrogen, E is CH and $Z^1$ is hydrogen;

$R^2$ is hydrogen;

$R^3$ is hydrogen or methyl;

$X^1$ is a bond;

Q is a group of formula IV in which $Z^2$ is hydrogen and $Z^3$ is hydrogen or a group of formula $X^2—G^a$ in which $X^2$ is oxymethylene and $G^a$ is carboxy;

$X^z$ is oxymethylene; and

G is carboxy, methoxycarbonyl, ethoxycarbonyl or t-butoxycarbonyl;

or a pharmaceutically acceptable salt thereof.

11. The method of claim 7 wherein $R^1$ represents a group of formula III in which T is CH and $X^3$ is ethylene;

$R^2$ is hydrogen;

$R^3$ is hydrogen or methyl;

$X^1$ is a bond;

Q is a group of formula IV in which $Z^2$ is hydrogen and $Z^3$ is hydrogen or a group of formula $X^2$—$G^a$ in which $X^2$ is oxymethylene and $G^a$ is carboxy;

$X^2$ is oxymethylene; and

G is carboxy, methoxycarbonyl, ethoxycarbonyl or t-butoxycarbonyl;

or a pharmaceutically acceptable salt thereof.

12. The method of claim 7 wherein the allophanic acid derivative of formula I is selected from: methy 14-[4-(-amidinophenyl)allophanoyl]phenoxyacetate and 4-[4-(-amidinophenyl)allophanoyl]phenoxyacetic acid; or a pharmaceutically acceptable salt thereof.

\* \* \* \* \*

UNITED STATES PATENT AND TRADEMARK OFFICE
CERTIFICATE OF CORRECTION

PATENT NO. : 5,494,922  
DATED : February 27, 1996  
INVENTOR(S) : Brown, et al

It is certified that error appears in the above-identified patent and that said Letters Patent is hereby corrected as shown below:

Col. 1, line 19, "yon" should be --von--.

Col. 4, line 39, "X2" should be --$X^2$--.

Col. 4, line 57, "X2" should be --$X^2$--.

Col. 5, line 4, "X2" should be --$X^2$--.

Col. 12, line 3, "allophoyl" should be --allophanoyl--.

Col. 13, line 9, "(H+H)$^+$" should be --(M+H)$^+$--.

Col. 13, line 10, "53.5Z;" should be --53.5%;--.

Col. 15, line 26 (Claim 1), "i or" should be --1 or--.

Col. 15, line 26 (Claim 1), "(1-4c) alkoxy" should be --(1-4C)alkoxy)--.

Col. 15, line 36 (Claim 1), "(1-4c)alkyl" should be --(1-4C)alkyl)--.

Col. 15, line 38 (Claim 1), "Iv" should be --IV--.

Col. 15, line 53 (Claim 1), "halogone," should be --halogeno,--.

Col. 15, line 53 (Claim 1), "(1-4c)alkyl," should be --(1-4C)alkyl,--.

UNITED STATES PATENT AND TRADEMARK OFFICE
CERTIFICATE OF CORRECTION

PATENT NO. : 5,494,922                                     Page 2 of 3
DATED      : February 27, 1996
INVENTOR(S) : Brown, et al It is certified that error appears in the above-identified patent and that said Letters Patent is hereby corrected as shown below:

Col. 15, line 61 (Claim 1), "(6-12c)aryl" should be --(6-12C)aryl)--.

Col. 17, line 4 (Claim 6), "4-[4-(-amidinophenyl)allophanoyl]phenoxyacetate" should be --4-[4-(4-amidinophenyl)allophanoyl]phenoxyacetate--.

Col. 17, line 5 (Claim 6), "4-[4-(-amidinophenyl)allophanoyl]phenoxyacetic" should be --4-[4-(4-amidinophenyl)allophanoyl]phenoxyacetic--.

Col. 17, line 28 (Claim 7), "(1-4c)alkoxy" should be --(1-4C)alkoxy)--.

Col. 17, line 40 (Claim 7), "(1-4c)alkylene" should be --(1-4C)alkylene)--.

Col. 17, line 63 (Claim 7), "(1-4c)alkylene" should be --(1-4C)alkylene)--.

Col. 17, line 65 (Claim 7), "Co" should be --CO--.

Col. 17, line 65 (Claim 7), "(1-6c)alkyl" should be --(1-6C)alkyl--.

Col. 18, line 5 (Claim 8), "pard" should be --para--.

Col. 18, line 25 (Claim 8), "or e" should be --or a--.

Col. 18, line 46 (Claim 10), "pare" should be --para--.

UNITED STATES PATENT AND TRADEMARK OFFICE
CERTIFICATE OF CORRECTION

PATENT NO.   :   5,494,922

DATED        :   February 27, 1996

INVENTOR(S)  :   Brown, et al

It is certified that error appears in the above-identified patent and that said Letters Patent is hereby corrected as shown below:

Col. 18, line 57 (Claim 10), "$X^z$" should be --$X^2$--.

Col. 20, lines 3-4 (Claim 12), ""4-[4-(-amidinophenyl)allophanoyl]phenoxyacetate" should be --4-[4-(4-amidinophenyl)allophanoyl]phenoxyacetate--.

Col. 20, line 4 (Claim 12), "4-[4-(-amidinophenyl)allophanoyl]phenoxyacetic" should be --4-[4-(4-amidinophenyl)allophanoyl]phenoxyacetic--.

Col. 20, line 3, "methy" should read --methyl--.

Signed and Sealed this

Twenty-fifth Day of June, 1996

Attest:

BRUCE LEHMAN

Attesting Officer    Commissioner of Patents and Trademarks